(12) United States Patent
Harmon et al.

(10) Patent No.: US 10,492,493 B2
(45) Date of Patent: Dec. 3, 2019

(54) BIRD DETERRENTS

(71) Applicant: B3 Solutions LLC, Overland Park, KS (US)

(72) Inventors: Bud Harmon, Wildwood, MO (US); Bob Baker, Overland Park, KS (US); James BeMiller, West Lafayette, IN (US)

(73) Assignee: B3 Solutions LLC, Overland Park, KS (US)

( * ) Notice: Subject to any disclaimer, the term of this patent is extended or adjusted under 35 U.S.C. 154(b) by 696 days.

(21) Appl. No.: 15/024,441

(22) PCT Filed: Sep. 26, 2014

(86) PCT No.: PCT/US2014/057730
§ 371 (c)(1),
(2) Date: Mar. 24, 2016

(87) PCT Pub. No.: WO2015/048451
PCT Pub. Date: Apr. 2, 2015

(65) Prior Publication Data
US 2016/0227773 A1    Aug. 11, 2016

Related U.S. Application Data

(60) Provisional application No. 61/883,564, filed on Sep. 27, 2013.

(51) Int. Cl.
| | | |
|---|---|---|
| *A01N 25/00* | (2006.01) | |
| *A01N 37/44* | (2006.01) | |
| *A01M 29/12* | (2011.01) | |
| *A01M 29/00* | (2011.01) | |
| *A01N 25/08* | (2006.01) | |
| *A01N 25/10* | (2006.01) | |
| *A01N 65/42* | (2009.01) | |

(52) U.S. Cl.
CPC ............. *A01N 37/44* (2013.01); *A01M 29/00* (2013.01); *A01M 29/12* (2013.01); *A01N 25/08* (2013.01); *A01N 25/10* (2013.01); *A01N 65/42* (2013.01)

(58) Field of Classification Search
CPC . Y10S 426/807; Y10S 426/806; A23K 20/24; A23K 40/20; A01M 29/12; A01N 37/44; A01N 25/08; A01N 25/10
USPC ........... 119/713; 426/807, 74, 623, 630, 635
See application file for complete search history.

(56) References Cited

U.S. PATENT DOCUMENTS

| | | |
|---|---|---|
| 2,955,981 A | 10/1960 | Linkenheimer |
| 2,967,128 A | 1/1961 | Kare |
| 3,259,500 A | 7/1966 | Bamhart et al. |
| 3,332,778 A | 7/1967 | Wilkening |
| 3,950,546 A | 4/1976 | Hill et al. |
| 4,016,296 A | 4/1977 | DeSantis |
| 4,027,043 A | 5/1977 | Schroeder et al. |
| 4,160,041 A | 7/1979 | Schroeder et al. |
| 4,171,379 A | 10/1979 | Harmon et al. |
| 4,171,385 A | 10/1979 | Skoch et al. |
| 4,171,386 A | 10/1979 | Skoch et al. |
| 4,234,608 A | 11/1980 | Linehan |
| 4,265,916 A | 5/1981 | Skoch et al. |
| 4,362,710 A | 12/1982 | Watanabe |
| 4,393,087 A | 7/1983 | Sullins et al. |
| 4,431,634 A | 2/1984 | Ellenbogen |
| 4,431,675 A | 2/1984 | Schroeder et al. |
| 4,455,304 A * | 6/1984 | Yaralian ................ A01N 65/00 424/405 |
| RE31,763 E | 12/1984 | Skoch et al. |
| RE31,804 E | 1/1985 | Skoch et al. |
| 4,686,105 A | 8/1987 | Dahlgren et al. |
| 4,708,877 A | 11/1987 | Donovan et al. |
| 4,735,809 A | 4/1988 | Donovan et al. |
| 4,749,578 A | 6/1988 | Benton et al. |
| 4,775,539 A | 10/1988 | Van de Walle |
| 4,798,727 A | 1/1989 | Miller |
| 4,800,088 A | 1/1989 | Sawhill |
| 4,800,092 A | 1/1989 | Miller |
| 4,826,694 A | 5/1989 | McAskie |
| 4,834,957 A | 5/1989 | Van de Walle |
| 4,851,244 A | 7/1989 | Theuninck et al. |
| 4,857,332 A | 8/1989 | Schricker |
| 4,869,907 A | 9/1989 | Sasagawa |
| 4,895,728 A | 1/1990 | Weakley et al. |
| 4,904,473 A | 2/1990 | Schricker et al. |
| 4,904,486 A | 2/1990 | Donovan et al. |
| 4,950,488 A | 8/1990 | Schweitzer et al. |
| 4,960,589 A | 10/1990 | Sasagawa |
| 4,963,371 A | 10/1990 | Miller |
| 4,976,963 A | 12/1990 | Schricker et al. |

(Continued)

FOREIGN PATENT DOCUMENTS

| | | |
|---|---|---|
| EP | 0173292 A2 | 3/1986 |
| WO | WO1992/016114 A1 | 10/1992 |

(Continued)

OTHER PUBLICATIONS

Borchardt, "Garlic Oil—An Organic, Environmentally Friendly Bird Repellent," The Maine Organic Farmer & Gardener (Spring 2005).

Hile et al., "Aversion of European Starlings (Sturnus vulgaris) to Garlic Oil Treated Granules: Garlic Oil as an Avian Repellent. Garlic Oil Analysis by Nuclear Magnetic Resonance Spectroscopy," J. Agric. Food Chem., vol. 52, pp. 2192-2196 (2004).

Mason et al., "Repellency of garlic extract to European starlings," Crop Protection, vol. 16, No. 2, pp. 107-108 (1997).

Primus et al., "Liquid Chromatographic Method for the Determination of Methyl Anthranilate in Liquid Formulation and Residues on Formulated Rice Seed Bait," J. Agric. Food Chem., vol. 43, pp. 3052-3056 (1995).

(Continued)

*Primary Examiner* — Yvonne R Abbott-Lewis
(74) *Attorney, Agent, or Firm* — Sonapat LLC

(57) ABSTRACT

Solid form compositions for deterring birds, methods for making such compositions and methods for deterring birds.

23 Claims, No Drawings

(56) References Cited

U.S. PATENT DOCUMENTS

| | | |
|---|---|---|
| 4,976,977 A | 12/1990 | Johnson et al. |
| 4,994,282 A | 2/1991 | Miller |
| 4,994,283 A | 2/1991 | Mehansho et al. |
| 4,996,065 A | 2/1991 | Van de Walle |
| 5,063,067 A | 11/1991 | Binder et al. |
| 5,073,388 A | 12/1991 | Miller |
| 5,165,946 A | 11/1992 | Taylor et al. |
| 5,187,196 A | 2/1993 | Cummings et al. |
| 5,242,690 A | 9/1993 | Moechnig |
| 5,260,089 A | 11/1993 | Thornberg |
| 5,264,017 A | 11/1993 | Van De Walle |
| 5,264,227 A | 11/1993 | Laroche et al. |
| 5,270,062 A | 12/1993 | Buchs |
| 5,296,226 A | 3/1994 | Askham |
| 5,356,650 A | 10/1994 | Kanayama |
| 5,378,471 A | 1/1995 | Smith |
| 5,416,115 A | 5/1995 | Erdman et al. |
| 5,549,902 A | 8/1996 | Preiser et al. |
| 5,744,178 A | 4/1998 | Ikeda et al. |
| 5,786,007 A | 7/1998 | Webb |
| 5,821,269 A † | 10/1998 | Blumberg |
| 5,879,696 A | 3/1999 | Blumberg |
| 5,922,373 A | 7/1999 | Johnston |
| 5,935,623 A | 8/1999 | Alonso-Debolt |
| 5,935,626 A | 8/1999 | Moechnig et al. |
| 5,997,939 A | 12/1999 | Moechnig et al. |
| 6,024,993 A | 2/2000 | Theuninck et al. |
| 6,143,333 A | 11/2000 | Lanter et al. |
| 6,168,803 B1 | 1/2001 | Harris et al. |
| 6,344,223 B1 | 2/2002 | Rekhif et al. |
| 6,387,419 B1 | 5/2002 | Christensen |
| 6,537,604 B1 | 3/2003 | Ethington, Jr. |
| 6,572,903 B1 | 6/2003 | Fuhr et al. |
| 6,726,941 B2 | 4/2004 | Ethington, Jr. et al. |
| 6,777,019 B1 | 8/2004 | Thornberg |
| 6,793,947 B2 | 9/2004 | Bachmeier |
| 6,824,788 B2 | 11/2004 | Summer et al. |
| 7,001,623 B2 | 2/2006 | Summer et al. |
| 7,279,616 B2 | 10/2007 | Freeman |
| 7,348,019 B1 | 3/2008 | Murphy et al. |
| 7,534,463 B1 | 5/2009 | Hall et al. |
| 9,351,944 B1 * | 5/2016 | Yamasaki ............. A61K 31/085 |
| 9,877,927 B2 * | 1/2018 | Namba ................ A61K 31/045 |
| 2002/0028283 A1 | 3/2002 | Freeman |
| 2006/0165622 A1 * | 7/2006 | Hiramoto ............... A61K 8/347 |
| | | 424/65 |
| 2011/0064834 A1 * | 3/2011 | Streisfeld ............... A01N 65/00 |
| | | 424/754 |
| 2012/0177755 A1 | 7/2012 | King |
| 2014/0127275 A1 * | 5/2014 | Cohen ................... A61K 8/731 |
| | | 424/401 |
| 2017/0156346 A1 * | 6/2017 | Groom .................. A01N 65/42 |
| 2019/0069576 A1 | 3/2019 | Harmon |

FOREIGN PATENT DOCUMENTS

| | | |
|---|---|---|
| WO | WO1999/026488 A1 | 6/1999 |
| WO | WO2017146672 | 8/2017 |
| WO | WO2017147084 | 8/2017 |

OTHER PUBLICATIONS

Werner et al., "Evaluation of Bird ShieldTM as a blackbird repellent in ripening rice and sunflower fields," Wildlife Society Bulletin, 33(1), pp. 251-257 (2005).

PCT International Search Report for PCT/US2014/057730, dated Dec. 29, 2014.

PCT Written Opinion for PCT/US2014/057730, dated Dec. 29, 2014.

\* cited by examiner
† cited by third party

BIRD DETERRENTS

Bird droppings are unsightly and mar or obscure the appearance of buildings, furniture, lawns, and fields to name a few areas. In addition, birds are viewed as pests in agriculture because they are responsible for losses in production. When undeterred, birds often build nests which are themselves unsightly and become repositories for microbes and cause further losses due to droppings and pest behavior. Birds are the greatest vector for disease transmission in most food-animal production systems and create considerable filth and microbe contamination in outside eating establishments. Numerous types of chemical bird deterrents have been proposed in the literature, however, these are usually of little or no effect. Chemicals which are toxic to humans should be avoided, and chemicals which are not toxic to humans suffer from a number of drawbacks including the inability to deliver an effective dose of deterrent over any appreciable area for sufficient time. For example, such chemicals are often distributed as gels and are only effective on surfaces where the gel is applied. Their effectiveness is further diminished in adverse weather conditions. Non-chemical means also exist but are of limited effectiveness. Mechanical means for deterring birds are often unsightly, such as spikes, nets or wires, and require extensive infrastructure to support an appreciable area. Visual scares and decoys also have only limited effectiveness. More recently, electronic bird controls have been employed, but they are expensive and have a limited radius due to the rapid dissipation of ultrasound frequencies over distance and there is debate in the literature as to their effectiveness. There is a need in the industry to provide for an effective deterrent of birds which is non-toxic, non-disruptive, and which can treat a sufficiently large area to deter birds such as by repelling birds or by limiting the feed intake of birds.

SUMMARY OF THE INVENTION

In one aspect of the invention, solid form bird deterrent compositions comprising a deterrent are provided.

A further aspect of the invention provides processes for making solid form bird deterrent compositions comprising a deterrent, which processes comprise combining a carbohydrate source, deterrent and one or more garlic substances, and a filler, to form a mixture and treating the mixture with a metal oxide to form a bird deterrent composition.

In additional aspects, methods for deterring birds with solid form bird deterrent compositions are provided herein.

In other aspects, methods for limiting the feed intake of birds by providing solid form bird deterrent composition of the invention are provided herein.

DETAILED DESCRIPTION

As used herein, the term "deterrent composition" or "bird deterrent composition" means a solid form composition that may be used to either repel birds or limit the feed intake of birds. For example, deterrent compositions of the invention may be used to limit feed intake of birds by discouraging them from consuming food sources. In some embodiments, for example, the deterrents may be placed directly in food sources thereby discouraging birds from consuming or over consuming such food sources. In such deterrent compositions, it is often convenient to use a solid form of a deterrent composition which is granular. In such embodiments, birds are deterred from consuming such food sources, which may cause birds to vacate a particular area and thus diminish or eliminate unsightly droppings and the disadvantages associated therewith.

Deterrent compositions may be used to repel birds and may or may not be placed in food sources. For example, in some embodiments, block forms of deterrent compositions have been shown to deter birds from nesting in areas where the blocks have been placed. It will be understood by those of skill in the art that, unless indicated otherwise, those compounds and substances that may be used to repel birds may also be used to limit feed intake by birds.

The bird deterrents used herein may be any suitable bird repellent. Non-toxic bird repellents are preferred and such bird repellents are known in the art. Examples of known bird repellents include, but are not limited to, those set forth in Table 1. Not all of the bird repellents of Table 1 are non-toxic.

TABLE 1

| Bird Repellents |
|---|
| Alcohols (e.g., 2-butoxyethanol, cinnamyl alcohol, (E)-2-hexen-1-ol, (E)-2-octenol, (Z)-3-octen-1-ol, phenoxyethanol, phenylethanol) |
| Aldehydes (e.g., cinnamyl aldehyde, cyclamen aldehyde, decanal, dodecanal, (E)-2-heptanal, (E)-2-hexanal, (Z)-hexenal, nonanal, (E)-2-octenal, octanal, undecanal) |
| Alkenes (e.g., monolefins, diolefins, cycloolefins, cyclodiolefins, polyalkenes) |
| Alkylamines |
| Allyl isothiocyanate |
| Anilines (e.g., p-chloro-, o-chloro-p-nitro-, 3,4-dichloro-, 2,6-dichloro-4-nitro-, 2,4,6-trichloro-) |
| Anthranilic acid, methyl, ethyl, and other alkyl esters of |
| Benzene derivatives (e.g., chlorodinitrobenzene, p-chloronitrobenzene, p-dichlorobenzene, dimethoxybenzene, dodecylbenzene) |
| Cinnamamide |
| Citronellyl compounds |
| Diallyl sulfide |
| Dibenzyl disulfides |
| Dimethyl- and diethyl anthranilate |
| Diphenyl and its derivatives (e.g., diethyl-, ethyl-, terphenyl) |
| Essential oils (e.g., camphor oil, cedar wood oil, cinnamon oil, corn mint oil, eucalyptus oil, Houttuyania cordata oil, jasmine oil, mint oil, mustard oil, neem oil, orange oil, peppermint oil, rose oil, rose geranium oil, rosemary oil, spearmint oil) |
| Esters (e.g., other alkyl esters of anthranilic acid, benzyl acetate, 1,1-dimethyl-2-phenyl acetate (dimethylbenzyl carbinol acetate), 1,1-dimethyl-2-phenylethyl acetate, dimethyl phthalate, ethyl methylphenylglycidate, methyl cinnamate, esters of phenylacetic acid, esters of salicylic acid (methyl, ethyl, propyl, butyl, isobutyl, isoamyl)) |

TABLE 1-continued

Bird Repellents

Ethers (e.g., dibenzyl ether, diethyleneglycol butyl ether acetate, diethyleneglycol ethyl ether acetate, diphenyl ether, methyl naphthyl ether)
Thio ethers (e.g., diphenyl thioether)
Heterocyles, 6- or 8-membered, S- or O-containing
Ketones (e.g., acetophenone and derivatives thereof (e.g., o-amino-, methoxy-), civetone, cyclohexanone, cyclopentadecanone, methyl amyl ketone, methyl nonyl ketone, methyl phenyl ketone)
Lactones (gamma-nonalactone, gamma-undecalactone)
Macrocycles (e.g., muscone)
Musk (e.g., musk M, musk T, and variations thereof)
Napthalene and its derivatives (e.g., dimethyl-, methyl-)
Phenols (e.g., cresols, 2,6-dicyclohexyl-4-methylphenol, 2,6-di(tert-butyl)-p-cresol, obtained from pyroligneous acid/wood tar)
Polycyclic quinones (e.g., 9,10-anthraquinone, dihydroxyanthraquinone, 2-methylanthraquinone)
Pyrimidines, methyl and ethyl derivatives of 4-amino-
Pyridine and its derivatives (e.g., 4-aminopyridine)
Smoke
Terpenes/terpenoids (e.g., borneol, camphor, carvone, citral, geraniol, dihydrogeraniol, limonene, linalool, tetrahydrolinalool, di-1-p-menthene, menthol, menthone and its derivatives, β-myrcene, pinene, pulegone)
S-Containing terpenes (e.g., thiogeraniol)
Tetrahydrothiphene
Vinegar, especially wood and bamboo vinegar
Wood distillates (e.g., creosote oil, wood tar)

Non-toxic deterrents themselves or in combination with garlic substances have been found to discourage and repel birds, but not harm them, from congregating at locations where their presence is harmful or unwanted. Although garlic itself is known as a bird deterrent, herein garlic has been found to work in combination with other bird deterrents in some embodiments to further achieve the benefits of the invention. For example, in some embodiments of the invention, the bird deterrent of the invention is methyl anthranilate. In some embodiments the methyl anthranilate has been prepared together with a garlic substance in a solid form composition and has been shown to deter birds. The solid form compositions may further be used to limit the food intake of birds. As used in the invention, the term "garlic substance" means any form of garlic and includes, but is not limited to, one or more of garlic powder, coarse garlic, garlic juice, garlic oil, or crushed garlic (wet or dry) including fresh garlic, whether crushed or not. Garlic substances may be provided with preservative levels of citric or similarly used acids. When coarse garlic is used, it is typically ground.

The compositions of the invention are delivered as solid forms which include blocks, granular materials, agglomerates, or materials intermediate between agglomerates and blocks. Agglomerated materials tend to be sticky and have a lower carbohydrate source content than blocks. Other solid forms include waxes and soaps. Solid forms, such as those in the shape of feed blocks are known in the art and have been used, for example, to provide feedstuffs to cattle and pigs. Such blocks, are meant to be hard and weather resistant and have been prepared with animal feed to deliver sources of energy and nutrients to animals. For example, U.S. Pat. No. 4,171,379, incorporated herein by reference, describes blocks which have been prepared with nutritional supplements for delivery to pigs. In the instant invention, solid forms in, for example, the shape of blocks, have been used not to deliver foodstuffs or other nutritional ingredients to animals, but to deliver bird deterrents or may be used to limit intake of feed where beneficial to do so. In many embodiments of the invention, the bird deterrent in the block solid forms have been magnified with the presence of one or more garlic substances. In other embodiments, solid form compositions in the form of blocks do not contain a garlic substance but do contain a deterrent such as methyl anthranilate. Such blocks, without a garlic substance, may contain a carbohydrate source, a filler, and a metal oxide. Blocks may also be ground to increase surface area. Agglomerates have a surface area that is intermediate between blocks and granular material with granular materials having the highest surface area.

In many embodiments of the invention, the solid form may be a granular material. Such granular materials may be used as bird deterrents as set forth herein. Such granular materials may be prepared by standard methods for making granular materials generally. Granular forms for limiting feed intake may be mixed with feed ingredients to form a complete feed for poultry species such as chickens, ducks, geese, turkeys, pheasants and quail. When present in such feed, the granular material reduces voluntary feed intake which leads to the advantage of minimizing obesity and other health problems such as during receding stages of the laying cycle, including molting and during pullet development to optimize growth and limit fat accretion. Similarly, the granular materials also herein referred to as a granular form, may be introduced into the feed of non-avian species, such as swine and cattle, to limit feed intake by wild birds. Thus, including a deterrent composition of the invention, particularly in granular form, will reduce feed consumption. Like in the block form, such granular forms may contain a deterrent or both a deterrent and a garlic substance. A common deterrent for the granular form, like the block and agglomerate solid forms, is methyl anthranilate. A typical garlic substance is coarse garlic.

The solid form compositions of the invention including block, granular, and agglomerate forms may further comprise a metal oxide and a carbohydrate source. A typical metal oxide is magnesium oxide. As used in the invention, carbohydrate sources include, but are not limited to, molasses, hemicellulose extracts, and lignon sulfonate salts such as sodium or ammonium salts. Molasses may be any commercial molasses product. For example, the molasses may be any of the sugar containing molasses such as those obtained as the by-products of the processing of sugar beets, sugar cane, corn or wood. Exemplary of these include blackstrap molasses, converted molasses, wood molasses, hydrol syrup, citrus molasses, and cane syrup molasses. Molasses has varying amounts of solids which affect its viscosity and the measure of the amount of such solids is normally given in the terms of Brix. With no intention to limit the present invention, for the consistency of the molasses that may be used has a wide variance, the Brix of commercially available molasses which may be used in the invention normally falls within the range of 60° Bx to 90° Bx. Other carbohydrate sources include wood or other extracts containing hemicelluloses. Hemicellulose extracts may be prepared by methods known in the art.

In these and other embodiments of the invention, the solid form, whether block, agglomerate granular, or others may also be prepared with fillers. Fillers of the invention include, but are not limited to, clays, wood fiber, pecan shells, peanut hulls, clays such as calcine and montmorillonite clay as well as sawdust, processed corn cobs, or ground corn cobs. The filler provides bulk and mass for the block so any suitable bulking agent may be used as a filler. Certain fillers may also act as adsorbents, such as processed corn cobs, ground peanut hulls and/or pecan shells, and may be incorporated into the solid form structure of the invention to provide a solid material within the solid form to adsorb the garlic substance and other deterrents for subsequent release from the solid form over time. Processed corn cobs, such as 10/20 sized may be used. Other sized processed corn cobs may also be used.

The solid form compositions of the invention, including the block, agglomerate, and granular forms, may also contain a phosphorus source. Such phosphorus sources are typically used as dispersants and may be used, for example, to disperse the fillers of the solid form composition. Examples of phosphorus sources include tetrasodium pyrophosphate and monoammonium phosphate. Other additives may also be used in the solid form compositions of the invention. For example, agents for promoting the formation of solid forms, typically as blocks, referred to as "promoting agents", may be used. Examples of such agents include, but are not limited to, animal and vegetable fats and oils. Typical oils include soybean oil, cottonseed oil, and fish oil. Fats include grease, bleachable fancy tallow, yellow grease, beef fat, lard, and the like. Setting agents may also be used, typically in the solid form block compositions of the invention. Setting agents quicken the setting time of the formation of the solid form during processing. A typical setting agent is ferrous sulfate. Any one or more of setting agents, promoting agents, or phosphorous agents may be used with the solid form compositions of the invention.

In several embodiments of the invention, solid form block compositions may contain methyl anthranilate, crushed garlic with citric acid and, optionally, garlic juice, and soybean oil. Peanut hulls, processed corn cobs, or pecan shells or both may be used as fillers and tetrasodium pyrophosphate and ferrous sulfate may also be used.

Those of skill in the art will recognize that in the embodiments herein, the ingredients used are often mixtures, solutions, or compositions. As such, the ingredients often contain other materials or impurities. For example, it is well known that molasses contains water. Thus, water is an intrinsic ingredient in many of the embodiments of the invention. In some cases, water is also purposefully added as described herein. When a composition is described as comprising components hereunder, it is understood that said composition is made by adding the ingredients as are typically available to one of ordinary skill in the art in the relative amounts where specified. Thus when a composition is described as having, for example, 60% hemicellulose extract, it is understood that that 60% may also contain other substances present in the hemicellulose extract such as water.

In some embodiments, a composition of the invention is a block comprising between about 10% and about 25% methyl anthranilate, and between about 1% and about 12% of one or more garlic substances selected from garlic juice and wet crushed garlic with citric acid by weight.

In some embodiments, a composition of the invention is a block comprising between about 2% and about 10% magnesium oxide, between about 15% and about 65% of a hemicellulose extract, between about 10% and about 25% methyl anthranilate, and between about 1% and about 12% of one or more garlic substances selected from garlic juice and wet crushed garlic with citric acid by weight.

In other embodiments, of the invention, a composition of the invention is a block comprising between about 10% and about 20% methyl anthranilate, and between about 10% and about 20% of one or more garlic substances. In some such embodiments, the garlic substance is coarse garlic.

In some embodiments, a composition of the invention is a block comprising between about 2% and about 5% magnesium oxide, between about 50% and about 65% of a hemicellulose extract, between about 10% and about 20% methyl anthranilate, and between about 10% and about 20% of one or more garlic substances by weight. In some such embodiments, the garlic substance is coarse garlic. Such embodiments may further comprise a filler selected from peanut hulls, processed corn cobs, pecan shells and clays. In some embodiments, the filler is processed corn cobs. The processed corn cobs may be present in an amount between about 3% and about 5% by weight.

In additional embodiments, a composition of the invention is a block comprising between about 2% and about 8% magnesium oxide, between about 15% and about 65% of a hemicellulose extract, between about 13% and about 23% methyl anthranilate, and between about 2% and about 5% of one or more garlic substances selected from garlic juice and wet crushed garlic with citric acid by weight.

In additional embodiments, a composition of the invention is a block comprising between about 5% and about 6% magnesium oxide, between about 15% and about 60% of a hemicellulose extract, between about 14% and about 18% methyl anthranilate, and between about 2% and about 5% of one or more garlic substances selected from garlic juice and wet crushed garlic with citric acid by weight.

In these and other embodiments, fillers, promoting agents, setting agents, a phosphorus source, and water may be included within the invention. For example, in some embodiments, fillers, such as those selected from peanut hulls and calcine clay, comprise between about 4% to about 7% by weight of the composition and a block promoting agent such as soybean oil between 0% and about 5% by weight of the composition of the invention. In such embodiments, water may comprise between 0% and about 10% of the composition of the invention, a phosphorus source such as tetrasodium pyrophosphate may be present between about 2% to about 3% of the composition of the invention, and a setting agent such as ferrous sulfate may be present in an amount between 0% and about 3% in the composition by weight.

In further embodiments, a composition of the invention may comprise a block comprising between about 2% and about 3% magnesium oxide, between about 60% and about 64% of a hemicellulose extract, between about 11% and about 16% methyl anthranilate, between about 10% and about 12% crushed garlic with citric acid, between about 3% and about 5% soybean oil, and between about 3.5% and about 5.5% ground peanut hulls or processed corn cobs. In additional embodiments, such compositions may comprise between about 1% and about 3% of tetrasodium pyrophosphate.

In some embodiments, a composition of the invention may comprise a block comprising between about 2.5% magnesium oxide, about 62% of a hemicellulose extract, about 12% methyl anthranilate, about 11% coarse crushed garlic with citric acid, about 4% soybean oil, and about 4.5% ground peanut hulls.

In other embodiments, bird deterrent compositions in the form of blocks may comprise coarse garlic present in an amount of about 10% to about 20% by weight or about 11% to about 19% by weight or about 12% to about 18% by weight or about 13% to about 17% by weight or about 14% to about 16% by weight including about 14% or about 15% by weight. In such embodiments, methyl anthranilate present in an amount of about 10% to about 20% by weight or about 11% to about 19% by weight or about 12% to about 18% by weight or about 13% to about 17% by weight or 14% to about 16% by weight including 14% or 15% by weight. In such embodiments, the blocks may further comprise hemicellulose extract between about 58% to about 62% by weight or about 59% to about 61% by weight including about 59% or about 59.1% by weight. In such embodiments, the blocks further comprise about 3.5% to about 5% processed corn cobs by weight, or about 4% or about 4.2% processed corn cobs by weight. Such embodiments further include between about 2% and about 3% by weight tetrasodium pyrophosphate including about 2.5% tetrasodium pyrophosphate by weight. Such embodiments may further comprise between about 4.5% and about 6% by weight magnesium oxide including about 5%, 5.1%, or 5.2% by weight.

When in granular form, the product may be packaged for commercial use in polylined bags. When in block form, the composition may be poured into a mold or cup to form a block during processing.

In some embodiments, a granular bird deterrent composition comprising a metal oxide and a carbohydrate source and wherein the deterrent is methyl anthranilate and wherein the garlic substance is selected from garlic, coarse garlic, garlic powder, garlic juice, or crushed garlic is provided. In some such embodiments, magnesium oxide is a metal oxide and hemicellulose extract is a carbohydrate source.

In other embodiments, a granular bird deterrent composition is provided wherein the deterrent is methyl anthranilate and is present between about 12% and about 18% by weight or between about 13% and about 17% by weight or between about 14% and about 16% including about 14% or about 15% or about 16% by weight. In such embodiments, the garlic substances are selected from coarse garlic or coarse garlic with garlic juice. The garlic substance in such embodiments are present at between about 12% and about 18% by weight or about 13% to about 17% by weight or about 14% to about 16% by weight including about 14% or about 15% or about 16% by weight. Such embodiments further comprise processed corn cobs at between about 58% to about 64% by weight or about 59% to about 63% or about 60% to about 62% including about 60%, about 61% or about 62%. In some such embodiments, the granular bird deterrent composition further comprises between about 1% and about 2% of a phosphorous source by weight selected from tetrasodium pyrophosphate and monoammonium phosphate, between about 5% and about 10% hemicellulose extract by weight or between about 6% and about 9% including about 6%, 7%, 8%, or about 9% by weight. Such embodiments further include between about 0.5% and about 2% magnesium oxide including about 0.6%, 0.7%, 0.8%, 0.9%, 1.0%, 1.1%, 1.2%, 1.3%, 1.4%, 1.5%, 1.6%, 1.7%, 1.8%, or about 1.9% by weight.

In additional embodiments for bird deterrent compositions in granular the form, coarse garlic is present in an amount of about 14% by weight, and methyl anthranilate present in an amount of about 15% by weight. In such embodiments, the granular form further comprises about 7% by weight hemicellulose extract, between about 61% and about 62% processed corn cobs by weight, about 1.5% tetrasodium pyrophosphate by weight, and about 0.9% magnesium oxide by weight. The corn cobs may also be present at about 61.6% by weight.

In the agglomerate form, embodiments include compositions comprising between about 32% and about 34% hemicellulose extract, about 15% methyl anthranilate, between about 10% and about 14% coarse garlic, between about 31% and about 35% processed corn cobs, between about 1.4% and about 1.9% tetrasodium pyrophosphate and between about 2% and about 5% magnesium oxide.

In other embodiments, the agglomerate form may comprise between about 32% and about 34% hemicellulose extract, about 15% methyl anthranilate, between about 10% and about 14% coarse garlic, about 23% to about 34.5% processed corn cobs, up to about 11% water, up to about 4% garlic juice, up to about 1.5% soy oil, between about 1.4% and about 1.9% tetrasodium pyrophosphate and between about 2% and about 5% magnesium oxide.

The solid forms of the invention have been found to deter birds such as swallows, geese, and buzzards and restrict feed intake. Other birds which may be deterred, including by restricting feed intake by the invention include, but are not limited to, pigeons, blackbirds, starlings, and sparrows.

Solid form bird deterrent compositions suitable for outdoor use are those which are sufficiently weather resistant to repel birds during or after inclement weather and are typically in the form of blocks. For example, in several embodiments of the invention, the solid form bird deterrent compositions have successfully repelled birds through inclement weather for over four months. While not necessary to repel birds for over four months to be weather resistant, repelling birds for such a period of time shows weather resistance. The block solid form of the invention may similarly be used to limit feed intake by placing blocks in close proximity to feed and feeders.

The invention also provides for processes for making solid form deterrent compositions.

In several embodiments of the invention, the carbohydrate source, such as a molasses or a hemicellulose extract is mixed with the deterrent and the one or more garlic substances and, optionally, a block promoting agent is also added to the mixture. The carbohydrate source is often heated to at least about 120 degrees Fahrenheit prior to mixing with the other components. Mixing may be achieved in a blender or Hobart type mixer. Fillers may then be added followed by the addition of a metal oxide such as magnesium oxide. A phosphorus source and a setting agent may also be added.

The addition of magnesium oxide in such embodiments is typically exothermic and causes the mixture to start to solidify.

In some embodiments, the filler is peanut hulls or processed corn cobs or both, the phosphorus source is tetrasodium pyrophosphate, and the block promoting agent is soybean oil.

After the addition of magnesium oxide, the mixture may be poured into a mold and cured and set within the mold. Curing may be done up to 12, 24, 36, or 48 hours. Typical curing temperatures are at least 120 degrees Fahrenheit. Setting may be done at elevated temperatures, room temperature, or below. One possible mold is a two-ounce cup which, after curing and setting, yields solid forms, such as blocks, of an approximate mass of less than about 125 grams typically, including less than about 100 grams. The size of the block is dependent on the amount of material made and the size of the mold or the cup. In many embodiments, blocks on the order of 40 g to 100 g were prepared including specific embodiments of 45 g, 50 g, 60 g and 100 g. Other intermediate block sizes were also prepared and can be prepared.

The invention further provides for deterring birds with solid form bird deterrent compositions described herein. These may be placed, for example, in the vicinity of areas of human traffic and food plant and animal production and processing sites to, for example, limit birds eating in the area or repel the birds and in either case rid the area of the filth accumulated in those congregating areas and the potential for microbial contamination and disease transmission caused by birds. Other uses are to reduce crop and feed loss. Solid form compositions, such as in the form of blocks, may be placed in proximity to, for example, any food animal production site for meat, milk and eggs, or feed production sites, vegetable and fruit production and processing sites, the periphery of farms, restaurants, sporting venues, statues and monuments, garden shops, and the periphery of homes or other areas or buildings frequented by birds for roosting, scavenging or feeding. When used in granular form, such compositions may be mixed with a food source. In many embodiments of the invention, the solid form ingredients are generally recognized as safe (GRAS) as determined by the Food and Drug Administration (FDA) or the Association of American Feed Control Officials (AAFCO).

In particular embodiments, blocks or granular forms containing about 15% methyl anthranilate and about 14% coarse garlic may be used to deter birds. For example, in such embodiments, such blocks having compositions 188, 191, 193, 194, and 194B may be used to repel birds whereas such granular forms having composition 194A may be used to limit feed intake of birds.

In other embodiments of the invention, the solid form may be made from a suitable organic acid salt and water. In such embodiments, the suitable organic acid salt may be the salt of a fatty acid such as a salt of stearic acid. One such salt is the sodium salt of stearic acid.

In embodiments using suitable organic acid salts and water, no carbohydrate source is required. In such embodiments, the amount of deterrent used is typically between about 12% and about 18% with an example of a deterrent being methyl anthranilate.

Many of the embodiments herein provide for ranges of components. When a range is provided, such as between about 10% and about 12% including about 10%, about 11%, or about 12%, for example, what is meant is that in one embodiment, the range about 10% to about 12% is provided, another embodiment is 10%, 11% another embodiment, and 12% yet another embodiment. All percentages herein are meant to be modified by the word "about" which is meant to incorporate usual and standard measurement variability as that term is well understood by those of skill in the art. Additional embodiments include the precise numerical values of any numbers modified by the word "about." For example, the disclosure of a range of between "about 10% and about 12%" includes the range of between 10% and 12%, and the disclosure of the value of "about 10%" includes 10%. Having generally described the invention, reference to certain examples, which are provided herein for purposes of illustration only, and are not intended to be limiting, unless otherwise specified, may be helpful to help to illustrate certain embodiments of the invention.

EXAMPLES

Preparation Example A

General Preparation of a solid form in the shape of a block using molasses as a carbohydrate source and without a bird repellent or a garlic substance (Examples 1-19). Such blocks may be made by a number of methods including those described in U.S. Pat. No. 4,171,379.

In one method, one combines molasses with filler (one or more of peanut hulls, processed corn cobs, clays, and wood fiber), water, soybean oil, and tetrasodium pyrophosphate in a Waring® blender. After mixing for about three minutes, magnesium oxide is slowly added as the mixture begins to solidify. The contents of the blender are poured quickly into molds such as pre-greased plastic cups and are capped with tops to minimize evaporation. The capped cups are cured at about 120° F. to cure for 12-72 hours or longer and then set at room temperature to cool. The blocks may then be taken out of the cups.

Preparation Example B

Preparation of blocks with methyl anthranilate (Examples 20-28)

In these examples, the general method of Preparation Example A is followed, but methyl anthranilate as indicated is added to the mixture prior to the addition of magnesium oxide. In some examples, the setting agent ferrous sulfate is also added prior to the addition of magnesium oxide.

Preparation Example C

Preparation of blocks using hemicellulose extract with methyl anthranilate (Examples 29-42)

In these examples, the general methods of A and B are followed except a hemicellulose extract (typically from wood molasses) is used as the carbohydrate source.

Preparation Example D

Preparation of blocks using hemicellulose extract with methyl anthranilate and a garlic substance (Examples 43-54, 96, 97, 129, 150, 154, 156, 158, 165, 174, 180, 181, 183, 187, 188, 191, 193, 194, and 194B). In examples 96 and 97 the blocks were placed in a refrigerator after reacting with magnesium oxide. Table 8 summarizes these examples beginning with example 96.

Hemicellulose extract (wood molasses) is heated to at least 120° F. and emptied into a Waring® blender. Methyl anthranilate, at room temperature or greater, crushed garlic with or without, as the case may be, citric acid, garlic juice, and soybean oil are combined and measured separately and then emptied into the Waring® blender. Water may optionally be added as well. The blender is started at a slow speed and gradually increased to about ⅔ of the speed of the blender and the contents are mixed for at least three minutes. Coarsely ground peanut hulls or processed corn cobs or wheat middlings, as the case may be, are slowly added to the Waring® blender and the blender speed is increased to full speed for three minutes. Tetrasodium pyrophosphate is slowly added (when present). Magnesium oxide is then slowly added and heat evolves from the blender as the material solidifies rapidly. The contents of the blender are poured quickly into pre-greased plastic cups and are capped with tops to minimize evaporation. The capped cups are cured at about 120° F. to cure for 48-72 hours or longer.

Table 2 summarizes the results of examples 1-19. These examples were made in general accordance with Preparation Example A. In these examples, the cure and dry temperatures were maintained for 12 to 24 hours. Each of examples 1-19 formed a solid block with varying degrees of hardness. The examples in Table 2 were prepared without methyl anthranilate or garlic substances.

TABLE 2

| Example # | 1 | 2 | 3 | 4 | 5 | 6 | 7 | 8 | 9 | 10 |
|---|---|---|---|---|---|---|---|---|---|---|
| Black Strap Molasses | 64 | 64 | 64 | 61 | 61 | 61 | 61 | 61 | 62 | 62.5 |
| Water | 14 | 14 | 14 | 14 | 15 | 14 | 16 | 16 | 14 | 12.5 |
| Peanut Hulls | 5 | 5 | 4 | 5 | 0 | 3 | 4 | 4 | 7 | 8 |
| Wood Fiber | 0 | 0 | 0 | 0 | 6 | 3 | 2 | 2 | 0 | 0 |
| Montmorillonite clay | 5 | 5 | 0 | 0 | 0 | 0 | 0 | 0 | 0 | 0 |
| Calcine clay | 6 | 6 | 6 | 6 | 6 | 6 | 6 | 6 | 6 | 6 |
| Tetra Na Pyrophosphate | 6 | 6 | 6 | 6 | 6 | 6 | 6 | 6 | 6 | 5 |
| Mixing time (min) | 4 | 2 | 2 | 3 | 5 | 5 | 5 | 4 | 4 | 4 |
| Magnesium Oxide 93HR | 6 | 6 | 6 | 8 | 6 | 7 | 6 | 6 | 6 | 5.5 |
| % | 100 | 100 | 100 | 100 | 100 | 100 | 100 | 100 | 100 | 100 |
| Mixing time (min) | 3 | 3 | 2 | 2 | 2 | 3 | 4 | 4 | 3 | 3 |
| Gram total | 100 | 100 | 200 | 200 | 200 | 200 | 200 | 200 | 200 | 200 |
| Cure and Dry Temp F. | 75 | 75 | 75 | 75 | 75 | 75 | 75 | 120 | 75 | 120 |

| Example # | 11 | 12 | 13 | 14 | 15 | 16 | 17 | 18 | 19 |
|---|---|---|---|---|---|---|---|---|---|
| Black Strap Molasses | 62.5 | 62.5 | 61 | 610 | 60 | 60 | 60 | 59 | 59 |
| Water | 12.5 | 12.5 | 12 | 12 | 12 | 11 | 9 | 7 | 7 |
| Peanut Hulls | 7 | 7 | 8 | 8 | 9 | 9 | 11 | 14 | 14 |
| Wood Fiber | 0 | 0 | 0 | 0 | 0 | 0 | 0 | 0 | 0 |
| Montmorillonite clay | 0 | 0 | 0 | 6 | 0 | 0 | 0 | 0 | 0 |
| Calcine clay | 6 | 6 | 6 | 0 | 7 | 7 | 7 | 7 | 7 |
| Tetra Na Pyrophosphate | 5 | 5 | 5.5 | 6 | 6 | 6 | 6 | 6 | 6 |
| Mixing time (min) | 4 | 4 | 4 | 4 | 4 | 4 | 4 | 4 | 4 |
| Magnesium Oxide 93HR | 6 | 6 | 6 | 6 | 6 | 7 | 7 | 7 | 7 |
| % | 100 | 100 | 100 | 100 | 100 | 100 | 100 | 100 | 100 |
| Mixing time (min) | 3 | 3 | 3 | 3 | 3 | 3 | 3 | 3 | 3 |
| Gram total | 200 | 200 | 200 | 200 | 200 | 200 | 200 | 200 | 200 |
| Cure and Dry Temp F. | 75 | 120 | 75 | 120 | 105 | 75 | 110 | 120 | 75 |

In Table 3, block bird repellent compositions were prepared using methyl anthranilate. No garlic substance was used in these examples. The general preparation followed Preparation Example B. Each of examples 20-28 formed blocks with varying degrees of hardness with the cane syrup block being less hard than the examples where black strap molasses was used. The cure and dry times for these examples was 24 hours. Additionally, in several of these examples the setting agent ferrous sulfate was added. Each example was placed into four 2-ounce solo cups as molds for the blocks.

TABLE 3

| Example # | 20 | 21 | 22 | 23 | 24 | 25 | 26 | 27 | 28 |
|---|---|---|---|---|---|---|---|---|---|
| Black Strap Molasses | 0 | 51 | 44 | 34 | 36 | 54 | 55 | 55 | 56 |
| Cane Syrup Molasses | 51 | 0 | 0 | 0 | 0 | 0 | 0 | 0 | 0 |
| Water | 6 | 4 | 10 | 28 | 25 | 10 | 10.5 | 12 | 5.5 |
| Methyl Anthranilate | 16 | 16 | 15 | 13 | 13 | 15 | 15 | 22 | 23 |
| Peanut Hulls | 11 | 11 | 11 | 9 | 9 | 5 | 5 | 3 | 4 |
| Calcine clay | 4.5 | 5.5 | 6 | 5 | 5 | 5 | 4 | 3 | 2.5 |
| Tetra Na Pyrophosphate | 5 | 5.5 | 5 | 4 | 4 | 5 | 4.5 | 4 | 3.5 |
| Ferrous Sulfate | 0 | 0 | 3 | 2 | 2.5 | 0 | 0 | 0 | 0 |
| Mixing time (min) | 5 | 5 | 3 | 2 | 3 | 3 | 3 | 3 | 3 |
| Magnesium Oxide | 6.5 | 7 | 6 | 5 | 5.5 | 6 | 6 | 6 | 5.5 |
| % | 100 | 100 | 100 | 100 | 100 | 100 | 100 | 100 | 100 |
| Mixing time (min) | 3 | 3 | 3 | 3 | 3 | 3 | 3 | 3 | 3 |
| Gram total | 200 | 228 | 200 | 262 | 242 | 200 | 200 | 200 | 200 |
| Filled 2-ounce Solo cups | 4 | 4 | 4 | 4 | 4 | 4 | 4 | 4 | 4 |
| Cure and Dry Temp F. | 120 | 120 | 120 | 120 | 120 | 120 | 120 | 120 | 120 |

In Table 4, Examples 29-38 hemicellulose extracts (wood molasses) were used as a carbohydrate source instead of a molasses. Methyl anthranilate without a garlic substance was used in these examples. As with the Table 2 examples, blocks were formed from two-ounce Solo® cups used as molds. The general process for preparing Examples 29-38 can be found in Preparation Example C.

TABLE 4

| Example # | 29 | 30 | 31 | 32 | 33 | 34 | 35 | 36 | 37 | 38 |
|---|---|---|---|---|---|---|---|---|---|---|
| Hemicellulose Extract | 55 | 55 | 50 | 56 | 56 | 58 | 59 | 60 | 60 | 61 |
| Water | 12 | 11 | 10 | 12 | 12 | 10 | 9.5 | 9.5 | 10 | 9 |
| Methyl Anthranilate | 15 | 15 | 15 | 15 | 15 | 15 | 15 | 15 | 15 | 15 |
| Peanut Hulls | 0 | 0 | 0 | 0 | 0 | 0 | 0 | 0 | 0 | 0 |
| Pecan Shells | 5 | 6 | 10 | 7 | 6 | 6 | 5 | 4 | 4 | 3.5 |
| Calcine clay | 3 | 3 | 3 | 1 | 1 | 1 | 1 | 1 | 1 | 1 |
| Tetra Na Pyrophosphate | 4 | 4 | 4 | 2 | 3 | 3 | 3 | 3 | 3 | 3 |
| Mixing time (min) | 4 | 3 | 2 | 2 | 2 | 2 | 3 | 3 | 4 | 3 |
| Magnesium Oxide | 6 | 6 | 6 | 7 | 7 | 7 | 7.5 | 7.5 | 7 | 7.5 |
| % | 100 | 100 | 100 | 100 | 100 | 100 | 100 | 100 | 100 | 100 |
| Mixing time (min) | 3 | 2 | 2 | 2 | 2 | 3 | 4 | 3 | 3 | 4 |
| Gram total | 200 | 200 | 200 | 200 | 200 | 200 | 200 | 200 | 258 | 420 |
| Filled 2-ounce Solo ® cups # | 4 | 4 | 4 | 4 | 4 | 4 | 4 | 4 | 4 | 7 |
| Cure and Dry Temp F. | 120 | 120 | 120 | 120 | 120 | 120 | 120 | 120 | 120 | 120 |

| Example # | 39 | 40 | 41 | 42 |
|---|---|---|---|---|
| Hemicellulose Extract | 60 | 52 | 62 | 60 |
| Water | 10 | 22 | 10 | 12 |
| Methyl Anthranilate | 15 | 15 | 15 | 15 |
| Peanut Hulls | 0 | 0 | 4 | 4 |
| Pecan Shells | 3.5 | 3 | 0 | 0 |
| Calcine clay | 1 | 0.5 | 0 | 0 |
| Tetra Na Pyrophosphate | 3 | 3 | 3 | 3 |
| Mixing time (min) | 4 | 2 | 3 | 3 |
| Magnesium Oxide | 7.5 | 4.5 | 6 | 6 |
| % | 100 | 100 | 100 | 100 |
| Mixing time (min) | 4 | 2 | 2 | 3 |
| Gram total | 422 | 221 | 200 | 200 |
| Filled 2-ounce Solo ® cups # | 7 | 4 | 4 | 4 |
| Cure and Dry Temp F. | 120 | 120 | 120 | 120 |

In Table 5, methyl anthranilate together with various garlic substances were combined in accordance with the general process of Preparation Example D. The mass of the blocks prepared hereunder are also set forth in Table 5. In Example 45, the cure and drying was with an open cover for 12 hours and then covered. For Example 46, no caps were on the cups for the first 6 hours, the caps were put on 3 cups. After 10 hours, caps were put on all cups.

TABLE 5

| Example # | 43 | 44 | 45 | 46 | 47 | 48 | 49 |
|---|---|---|---|---|---|---|---|
| Hemicellulose Extract | 59 | 59 | 59 | 59 | 55 | 55 | 55 |
| Water | 10 | 8 | 8 | 10 | 5 | 3 | 3 |
| Garlic Powder | 3 | 5 | 5 | 5 | 0 | 0 | 0 |
| Garlic Juice | 0 | 0 | 0 | 0 | 0 | 0 | 0 |
| Wet Crushed Garlic with citric acid &w/o | 0 | 0 | 0 | 0 | 13 | 14 | 14 |
| Methyl Anthranilate | 15 | 15 | 15 | 15 | 15 | 15 | 15 |
| Soy bean oil | 0 | 0 | 0 | 0 | 0 | 0 | 0 |
| Peanut Hulls | 4 | 4 | 4 | 4 | 4 | 4 | 4 |
| Calcine clay | 0 | 0 | 0 | 0 | 0 | 0 | 0 |
| Tetra Na Pyrophosphate | 3 | 3 | 3 | 3 | 3 | 3 | 3 |
| Mixing time (min) | 3 | 3 | 3 | 3 | 3 | 3 | 3 |
| Magnesium Oxide | 6 | 6 | 6 | 6 | 5.5 | 6 | 6 |
| % | 100 | 100 | 100 | 100 | 100 | 100 | 100 |
| Mixing time (min) | 3 | 3 | 3 | 3 | 3 | 3 | 3 |
| Gram total | 300 | 300 | 300 | 300 | 300 | 300 | 300 |
| Filled 2-ounce Solo ® cups # | 6 | 6 | 5 | 6 | 6 | 6 | 6 |
| Approx. gm. per cup | 45 | 45 | 50 | 45 | 45 | 45 | 45 |
| Cure and Dry Temp F. | 120 | 120 | 110 | 120 | 110 | 120 | 120 |

| Example # | 50 | 51 | 52 | 53 | 54 |
|---|---|---|---|---|---|
| Hemicellulose Extract | 54 | 54 | 54 | 51 | 50 |
| Water | 0 | 0 | 0 | 0 | 0 |
| Garlic Powder | 0 | 0 | 0 | 0 | 0 |
| Garlic Juice | 0 | 3 | 3 | 3 | 2 |
| Wet Crushed Garlic with citric acid &w/o | 15 | 12 | 12 | 12 | 15 |
| Methyl Anthranilate | 14 | 14 | 14 | 15 | 14 |
| Soy bean oil | 4 | 4 | 4 | 5 | 4 |
| Peanut Hulls | 4 | 4 | 4 | 5 | 4 |
| Calcine clay | 0 | 0 | 0 | 0 | 3 |
| Tetra Na Pyrophosphate | 3 | 3 | 3 | 3 | 2 |
| Mixing time (min) | 3 | 3 | 3 | 3 | 3 |
| Magnesium Oxide | 6 | 6 | 6 | 6 | 6 |
| % | 100 | 100 | 100 | 100 | 100 |
| Mixing time (min) | 3 | 3 | 3 | 3 | 3 |
| Gram total | 315 | 352 | 451 | 343 | 370 |

TABLE 5-continued

| Filled 2-ounce Solo ® cups # | 6 | 3 | 2 | 3 | 3 |
|---|---|---|---|---|---|
| Approx. gm. per cup | 45 | 100 | 204 | 105 | 110 |
| Cure and Dry Temp F. | 120 | 120 | 120 | 120 | 120 |

Example I

On day 1, a single 41 g block of Example 31 was cut in half and placed under the roof in the front porch of one of the inventors. Three bird droppings were identified on day 2. No bird droppings were observed even after over 90 days. After 40 days, the weight of the two blocks had dropped to 31 grams.

Example II

On day 1, two 50 gram blocks of Example 33 were placed on plastic spikes near the front porch of a 2-story vestibule. It had been observed that swallows had nested and perched near the front porch ceiling for many years and had defecated frequently in that area during that period. Birds develop a habit of scrounging feed and then returning to a selected area to chew and swallow the feed. Eating by birds is more than a prehensile activity. Birds rather quickly pass intake to the crop where the eating process continues, much of which may occurs after devouring the food and returning to a common roosting site and physical break down continues in the gizzard. The floor of the porch was washed thoroughly on day 1 to make the identification of feces easy. After eleven months, no swallows have been perching in the area nor have any feces been observed.

Example III

Four 50 g blocks were prepared from Examples 34, 35, 36, and 37 respectively. On day 1, the block from Example 34 was placed under a soffit adjacent to a down spout at a residential house alongside a sparrow nest. Within three days, the sparrows had abandoned the nest. The other 3 blocks were placed along the top of a fence used by birds that roosted and ate feed scrounged in the immediate area. After placement of blocks, birds stopped eating and defecating in that area. After placement, birds stopped roosting on the fence.

Example IV

Two 50 gram blocks of Example 38 were prepared and on day 1, they were hung under a roof in a boat dock on a lake. The area of the dock was measured to be about 600 square feet. Swallows have been known to eat, nest and roost in under security of docks for some years with roosting to be an extension of eating beyond simply prehensile intake of feed. Just prior to block placement, the floor was cleaned. The swallows left the boat dock and no evidence of a return has been seen after over a year.

Example V

Two 50 gram blocks of Example 44 were placed under the second story deck on day 1 of a residential house where swallows had nested for years. The swallows abandoned the nest within four days and as of day 75 had not returned.

Example VI (Stability)

One 39 gram block of Example 49 was put in a plastic bag and hung in a bush in the yard of a residential house. Some weight was lost, but about half of the block remained even after one year.

Example VII (Stability)

One 88 gram block of Example 51 was wrapped in mesh bag and hung in Dogwood tree in open area in back of a residential house. After about 5 months, it was estimated that over 60% of the block remained.

Example VIII

On day 1, five 50 gram blocks of Example 50 and a 110 gram block of Example 54 were positioned at the top of a 50-ft feed mill elevator leg where for months an estimated large number of 50 plus buzzards have been seen on the tower, guy wires and immediate vicinity in the mornings. On day 2, only a single buzzard was seen. No buzzards have been seen for over a year around the feed mill since application of the blocks while the buzzards continue to maintain a habitat approximately a mile away.

Preparation Example E

Blocks of the following formula:
a. Hemicellulose extract from wood molasses: 62%
b. Methyl Anthranilate: 12%
c. Coarse Crushed Garlic (with a citric acid preservative): 11%
d. Soybean Oil: 4%
e. Ground peanut hulls: 4.5%
f. Magnesium Oxide: 2.5%
were prepared in accordance with Example D. Curing and drying temperatures of about 110° F. to about 120° F. (added) were used.

Preparation Example F

General Preparation of Blocks containing sodium stearate
Sodium stearate was mixed with water. The mixture was heated until a plastic mass formed. Garlic paste containing citric acid methyl anthranilate, or both (depending on the Example) were added and mixed into the hot mass, which was then placed in a 4-ounce plastic cup. The mass quickly hardened upon cooling.

Preparation Examples G

Using the general preparation set forth in Preparation Example E, mixtures and blocks with the following compositions set forth in Table 6 were prepared (by weight):

TABLE 6

| Example | 65 | 66 | 67 | 68 | 69 | 70 | 71 |
|---|---|---|---|---|---|---|---|
| % Sodium Stearate | 15 | 15 | 14 | 28 | 25 | 24 | 26 |
| % Water | 83 | 78 | 77 | 65 | 59 | 57 | 61 |
| % Garlic Paste | 0 | 7 | 7 | 0 | 16 | 16 | 0 |
| % Methyl Anthranilate | 2 | 0 | 1.5 | 7 | 0 | 3 | 13 |

Using the general preparation set forth in Preparation Example D, mixtures and blocks with the following compositions set forth in Table 7 were prepared (by weight). All cure temperatures were at about 120 degrees Fahrenheit.

Preparation Example H

General preparation method for making granular materials (Examples 127, 141, 142, and 194A)
Dry ingredients (processed corn cobs, magnesium oxide, and tetrasodium pyrophosphate) are put into the feed mixer in descending order from ingredient with the greatest concentration down to the ingredients of lowest concentration in a Hobart mixer, paddle mixer, ribbon mixer, or auger mixer. Once the dry ingredients are put in mixer and allowed to mix for about 90 to 150 seconds, then the liquid ingredients are added (coarse garlic, hemicellulose extract, methyl anthranilate). The total formula is allowed to mix for about 2 to 3 minutes. The granular product will usually contain particles of 3 to 6 mesh size. In Example 127, garlic juice was added with the liquid ingredients. Table 9 summarizes the granular materials made hereunder.

Example IX

On day one, four (4) 60 gram blocks of Example 150 were placed in trees and under a covered deck adjacent to residence swimming pool. Prior to blocks being placed bird droppings were cleaned from covered patio and deck area 3-4 times a week. Within three days of the blocks being placed, the area was mostly free of bird droppings. The area was cleaned again and was not cleaned of bird droppings thereafter. The homeowner expressed that the birds were not in that area after the fourth day of the blocks being placed. One month later, the blocks placed in the trees were accidentally removed by tree trimmers, however the remaining blocks maintained a bird free environment. After four months, the birds had not returned, and the blocks under the covered deck have maintained roughly 80% of their original volume.

Example X

On day one, six (60 gram) blocks of Example 129 were placed on window sills of a homeowner who had complained of birds pecking on the windows. Blocks were also placed adjacent to the windows. Within five days the pecking had stopped. After five months, the blocks were in place and the birds had not returned.

Example XI

A homeowner had complained that a patio area with overhanging limbs of trees was continually covered with bird droppings. On day one, three (3) 60 gram blocks from example 129 were placed roughly ten feet apart in a nearby tree. After two days there was a reduction in the droppings and within five days, the droppings had been eradicated and over the next four months, there was only one instance of a single bird dropping. After four months, the blocks maintained about 60-70% of their original size.

Example XII

A homeowner had a fence that birds were roosting on continually and leaving large amounts of droppings all over the fence. The fence span was roughly 80 ft. long and 4 feet tall. Before placement, the fence was power washed of all droppings. One (1) sixty gram agglomerate of Example 143 was placed at the intersection of the top rail and each fencepost. A total of eight agglomerates from Example 143 were used to cover the eighty foot span. On day four, 80%-90% of the birds were observed to no longer be roosting on the fence. By day six, the birds had stopped roosting on the fence. The fence was cleaned once more and has remained clean for over 150 days. The agglomerates were completely exposed to the elements and over the 150 days were reduced to roughly 10%-15% of their original size.

Example XIII

In this example a rehabilitation center for horses had a barn that was infested with barn swallows. The barn measured about 150 feet long with a width of 60 feet for approximately half of that length, narrowing to about 30 feet for the remainder. Prior to placing any blocks, the barn was power washed to remove as many bird droppings as possible. The wider half of the barn was treated with thirty-three (33) sixty gram blocks of Example 40. The blocks were placed roughly 10-15 ft. apart on the rafter joists overhead. The blocks were placed on every second or third joist apart from each other to maintain the 10-15 foot separation. The narrower half of the barn was not treated. The end that contained blocks had a large window at the end of the barn where circulating air could enter the barn. The barn owner reported that after about five days, days the number of birds had dropped by roughly 90% in the part of the barn where the blocks were placed. Near a large door on the side of the barn that was not treated, the barn owner noticed that there were still some birds present. Roughly three weeks later eight additional blocks were placed around the large barn door and it was reported the additional blocks cleared the remaining area of birds. The blocks lasted roughly 8 months in this environment.

Example XIV

A feed mill reported bird infestations on porch areas where bags of various feeds were stored requiring weekly cleanings due to bird droppings and damage done to feed bags by the birds. Sixteen 60 gram blocks of Examples 96 and 97 were placed in proximity to the affected area roughly ten feet apart. Within about a week, the bird infestation had ended and no more cleanings of the porch were required. The original blocks had an average starting weight of 76.9 grams, and ending weight of 41.4 grams. These blocks were primarily placed in locations that were out of direct weather.

Preparation Example J

Making agglomerated solid forms (Examples 140, 143, 151, and 152)

The general process of Preparation Example D is followed with the amounts of ingredients as set forth in Table 10 except that the final product was prepared in a cookie sheet rather than in cups.

Example XV

A granular solid form of the invention is analyzed and contains the following ingredients by weight:

| | |
|---|---|
| Crude Protein (Min) | 1.8% |
| Crude Fat (Min) | 0.2% |
| Crude Fiber (Max) | 22.0% |
| Calcium (Min) | 0.2% |
| Calcium (Max) | 0.5% |
| Phosphorus | 0.2% |

Example XVI (Prophetic)

A block solid form of the invention is analyzed and contains the following ingredients by weight:

| | |
|---|---|
| Crude Protein (Min) | 1.4% |
| Crude Fat (Min) | 0.2% |
| Crude Fiber (Max) | 7.7% |
| Calcium (Min) | 0.2% |
| Calcium (Max) | 0.5% |
| Phosphorus | 0.2% |

TABLE 7

| Example | 72 | 73 | 74 | 75 | 76 | 77 | 78 | 79 | 80 |
|---|---|---|---|---|---|---|---|---|---|
| Hemicellulose Ext | 51.5 | 52 | 52 | 52.5 | 62 | 62 | 62 | 62 | 62.5 |
| Methyl Anthranilate | 15 | 15 | 15 | 15 | 12 | 12 | 12 | 12 | 12 |
| CrsCrushGarlic W/CIT | 0 | 15 | 0 | 0 | 11 | 0 | 11 | 0 | 11 |
| CrsCrushGarlic W/O CIT | 14.5 | 0 | 15 | 15 | 0 | 11 | 0 | 11 | 0 |
| Garlic Juice | 3.5 | 4.0 | 4.0 | 5.0 | 4.0 | 4.0 | 4.0 | 4.0 | 4.0 |
| Peanut hulls unregrnd | 4.5 | 3.5 | 3.5 | 4.0 | 4.0 | 4.0 | 4.5 | 4.5 | 5.0 |
| Soybean Oil | 3.0 | 4.0 | 4.0 | 4.0 | 4.0 | 4.0 | 4.0 | 4.0 | 4.0 |
| Calcine | .5 | 0 | 0 | 0 | 0 | 0 | 0 | 0 | 0 |
| Tet Na PO4 | 1.5 | 1.5 | 1.5 | 0.5 | 0.5 | 0.5 | 0 | 0 | 0 |
| Mg Oxide | 6.0 | 5.0 | 5.0 | 5.0 | 2.5 | 2.5 | 2.5 | 2.5 | 2.5 |
| % | 100 | 100 | 100 | 100 | 100 | 100 | 100 | 100 | 100 |
| Gram total | 400 | 400 | 400 | 400 | 200 | 400 | 400 | 400 | 400 |
| Cups | 7 | 7 | 7 | 7 | 4 | 7 | 7 | 2/100 3/50 | 7 |
| Gms/cup | 50 | 50 | 50 | 50 | 50 | 50 | 50 | — | 50 |
| Caps on Cups | Y | Y | Y | Y | N | Y | Y | | |
| Caps on Cups | Y | Y | Y | Y | N | Y | Y | Y | Y |
| Delay in Caps | 0 | 0 | 0 | 0 | 0 | Aft 30 min | 0 | Aft 30 min | Aft 30 min |

Table 8—Blocks (96, 97, 129, 150, 154, 156, 158, 165, and 174)

TABLE 8

| Example | 96 | 97 | 129 | 150 | 154 | 156 | 158 | 165 | 174 |
|---|---|---|---|---|---|---|---|---|---|
| Water | | | | | 1 | 1 | 1 | 1.2 | 1.1 |
| Hemicellulose Extract | 58.5 | 57.5 | 56.7 | 59.7 | 59.7 | 59.6 | 59.7 | 59.2 | 59 |
| Methyl Anthranilate | 13 | 13 | 14.5 | 15 | 15 | 15 | 15 | 15 | 15 |
| Coarse Ground Garlic | 12 | 12 | 12 | 11 | 14 | 14 | 14 | 14 | 14 |
| Garlic Juice | 5 | 5 | 4.8 | 4 | | | | | |
| Proc Corn Cobs 10/20 | | | | 4 | 4 | 4 | 4 | 4.2 | 4.2 |
| Wheat middlings | | | 4 | | | | | | |
| Soybean Oil | 4 | 5 | 3.7 | | | | | | |
| Peanut hulls | 5 | 5 | | | | | | | |
| TetraNaPyroPO4 | 0.5 | 0.5 | 1.3 | 1.3 | 1.3 | 1.4 | 1.3 | 1.4 | 1.5 |
| Magnesium Oxide | 2 | 2 | 3 | 5 | 5 | 5 | 5 | 5 | 5.2 |
| % | 100 | 100 | 100 | 100 | 100 | 100 | 100 | 100 | 100 |
| Gram total | 400 | 400 | 400 | 400 | 400 | 400 | 922 | 500 | 520 |
| CureDry Temp F. | 115 | 115 | | | | | | | |

| Example | 180 | 181 | 183 | 187 | 188 | 191 | 193 | 194 | 194B |
|---|---|---|---|---|---|---|---|---|---|
| Water | 1.1 | 1.1 | 1.1 | 1.1 | 1.1 | 1.1 | | | |
| Lignon sulfonate Na | | | | | | | | 59.00 | |
| Lignon sulfonate NH4 | | | | | | | 59.1 | | |
| Hemicellulose Extract | 59 | 59 | 59 | 59 | 59 | 59 | | | 59.1 |
| Methyl Anthranilate | 15 | 15 | 15 | 15 | 15 | 15 | 15 | 15 | 15 |
| Coarse Ground Garlic | 14 | 14 | 14 | 14 | 14 | 14 | 14 | 14 | 14 |
| Proc Corn Cobs 10/20 | 4.2 | 4.2 | 4.2 | 4.2 | 4.2 | 4.2 | 4.2 | 4.2 | 4.2 |
| TetraNaPyroPO4 | 1.5 | 1.5 | 1.5 | 1.5 | 1.5 | 1.5 | 2.5 | 2.5 | 2.5 |
| Magnesium Oxide | 5.2 | 5.2 | 5.2 | 5.2 | 5.2 | 5.2 | 5.2 | 5.3 | 5.2 |
| % | 100 | 100 | 100 | 100 | 100 | 100 | 100 | 100 | |
| Gram total | 530 | 530 | 600 | 530 | 600 | 600 | 600 | 620 | |

Table 8 Cont.—Blocks (180, 181, 183, 187, 188, 191, 193, 194, and 194B)

Table 9—Granular (Examples 127, 141, 142, 194A)

TABLE 9

|  | Example | | | |
| --- | --- | --- | --- | --- |
|  | 127 | 141 | 142 | 194A |
| Water |  |  |  |  |
| Hemicellulose Extract | 7 | 8 | 6 | 7 |
| Methyl Anthranilate | 15 | 15 | 15 | 15 |
| Coarse Ground Garlic | 11 | 14 | 14 | 14 |
| Garlic Juice | 4 |  |  |  |
| Proc Corn Cobs 10/20 | 61 | 60.6 | 62.6 | 61.6 |
| TetraNaPyroPO4 | 1.3 | 1.5 | 1.5 | 1.5 |
| Magnesium Oxide | 0.7 | 1.9 | 0.9 | 0.9 |
| % | 100 | 100 | 100 | 100 |
| Gram total | 100 | 300 | 300 |  |

Table 10 Agglomerates (examples 140, 143, 151, and 152)

TABLE 10

|  | Example | | | |
| --- | --- | --- | --- | --- |
|  | 140 | 143 | 151 | 152 |
| Water |  |  |  | 11 |
| Hemicellulose Extract | 32.5 | 33.4 | 34 | 34 |
| Methyl Anthranilate | 15 | 15 | 15 | 15 |
| Coarse Ground Garlic | 13 | 14 | 10 | 11 |
| Garlic Juice |  |  | 4 |  |
| Proc Corn Cobs 10/20 | 34.1 | 33.5 | 31.3 | 23 |
| Soybean Oil | 1.5 |  |  |  |
| TetraNaPyroPO4 | 1.9 | 1.9 | 1.7 | 1.4 |
| Magnesium Oxide | 2 | 2.2 | 4 | 4.6 |
| % | 100 | 100 | 100 | 100 |
| Gram total | 300 | 350 | 400 | 400 |

We claim:

1. A solid form bird deterrent composition comprising a deterrent, a metal oxide, a carbohydrate source and a garlic substance, wherein the deterrent is methyl anthranilate and wherein the garlic substance is garlic, coarse garlic, garlic powder, garlic juice, or crushed garlic in the solid form composition.

2. The composition of claim 1, wherein the metal oxide is magnesium oxide and the carbohydrate source is a molasses or a hemicellulose extract.

3. The composition of claim 2, wherein the carbohydrate source is a hemicellulose extract.

4. The composition of claim 3, further comprising one or more fillers wherein the fillers are clays, wood fiber, ground pecan shells, processed corn cobs, or peanut hulls.

5. The composition of claim 4, further comprising a phosphorous source.

6. The composition of claim 5, wherein the phosphorous source is tetrasodium pyrophosphate or monoammonium phosphate.

7. The bird deterrent composition of claim 1, wherein the solid form deterrent composition is a block and wherein the deterrent is methyl anthranilate and is present between about 10% and about 20% by weight and wherein the garlic substance is present between about 10% and about 20% by weight.

8. The bird deterrent composition of claim 7, further comprising between about 2% and about 5% magnesium oxide, between about 1% and about 3% of tetrasodium pyrophosphate, and between about 50% and about 65% of hemicellulose extract.

9. The composition of claim 8, further comprising one or more fillers where the fillers are peanut hulls, processed corn cobs, pecan shells or clays.

10. The composition of claim 9, wherein the filler is processed corn cobs.

11. The composition of claim 10, wherein the processed corn cobs are present in an amount between about 3% and about 5%.

12. The bird deterrent composition of claim 1, wherein the solid form is a granular form.

13. The bird deterrent composition of claim 12, wherein the garlic substance is coarse garlic.

14. The bird deterrent composition of claim 13, wherein the metal oxide is magnesium oxide, the carbohydrate source is hemicellulose extract and further comprising a filler and a phosphorous source.

15. The bird deterrent composition of claim 14, wherein the filler is processed corn cobs and the phosphorous source is tetrasodium pyrophosphate or monoammonium phosphate.

16. The bird deterrent composition of claim 13, wherein the methyl anthranilate is present between about 12% and about 18% by weight and wherein the coarse garlic is present between about 12% and about 18% by weight and further comprising processed corn cobs at between about 60% to about 63% by weight.

17. The bird deterrent composition of claim 16, further comprising between about 1% and about 2% of a phosphorous source by weight selected from tetrasodium pyrophosphate and monoammonium phosphate, between about 5% and about 10% hemicellulose extract by weight, and between about 0.5% and about 2% magnesium oxide by weight.

18. The bird deterrent composition of claim 17, wherein the methyl anthranilate is present between about 14% and about 15% by weight, and the coarse garlic between about 14% and about 15% by weight.

19. The bird deterrent composition of claim 12, further comprising a garlic substance wherein the garlic substance is coarse garlic present in an amount of about 14% by weight, the deterrent is methyl anthranilate present in an amount of about 15% by weight and further comprising about 7% by weight hemicellulose extract by weight, between about 61° A and about 62% processed corn cobs by weight, about 1.5% tetrasodium pyrophosphate by weight, and about 0.9% magnesium oxide by weight.

20. The bird deterrent composition of claim 19, wherein the processed corn cobs are present in an amount of about 61.6% by weight.

21. A method of limiting bird feed intake comprising combining a granular composition of claim 19 with a food source.

22. The bird deterrent composition of claim 1, wherein the solid form is a block, further comprising a garlic substance wherein the garlic substance is coarse garlic present in an amount of about 14% by weight, the deterrent is methyl anthranilate present in an amount of about 15% by weight and further comprising between about 59% to 59.1% by weight hemicellulose extract, about 4.2% processed corn cobs by weight, about 2.5% tetrasodium pyrophosphate by weight, and about 5.2% magnesium oxide by weight.

23. A method of repelling birds comprising placing one or more deterrent compositions of claim 22 on or near exposed surfaces in need of bird repelling.

* * * * *